United States Patent [19]

Cannata et al.

[11] Patent Number: 4,622,419
[45] Date of Patent: Nov. 11, 1986

[54] PROCESS FOR THE OPTICAL RESOLUTION OF RACEMIC MIXTURES OF α-NAPHTHYL-PROPIONIC ACIDS

[75] Inventors: Vincenzo Cannata; Giancarlo Tamerlani, both of Pontecchio Marconi, Italy

[73] Assignee: Alfa Chemicals Italiana S.p.A., Milan, Italy

[21] Appl. No.: 795,516

[22] Filed: Nov. 6, 1985

[30] Foreign Application Priority Data

Nov. 22, 1984 [IT] Italy ............................. 23689 A/84

[51] Int. Cl.⁴ ...................... C07B 57/00; C07C 103/26
[52] U.S. Cl. ................................ 562/401; 260/544 B; 560/56; 562/402; 564/172
[58] Field of Search .................. 562/401, 402; 564/172

[56] References Cited

U.S. PATENT DOCUMENTS 4,246,164  1/1981  Felder et al. .................... 562/401 X
4,399,284  8/1983  Cannata et al. ................. 562/401 X Primary Examiner—Natalie Trousof
Assistant Examiner—Vera C. Clarke
Attorney, Agent, or Firm—Bucknam and Archer

[57] ABSTRACT

A process for the optical resolution of racemic mixtures of α-naphthyl-propionic acids of formula I

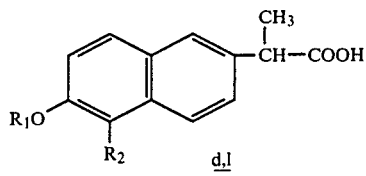

which consists of reacting a racemic mixture of a compound of formula II

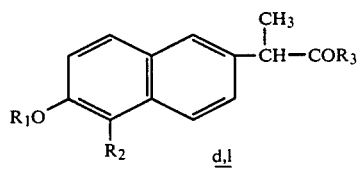

with an optically active compound of formula III $R_4$—$NH_2$ wherein $R_4$ is the residue of a primary or secondary alcohol which, taken with the $NH_2$ radical, forms an optically active β-aminoalcohol, to give a pair of diastereoisomeric amides, which is resolved into the single diastereoisomeric amides. Acid hydrolysis gives the optically active d or l α-naphthyl-propionic acids. The meaning of $R_1$, $R_2$, $R_3$ is given.

18 Claims, No Drawings

PROCESS FOR THE OPTICAL RESOLUTION OF RACEMIC MIXTURES OF α-NAPHTHYL-PROPIONIC ACIDS

BACKGROUND OF THE INVENTION

The α-naphthyl-propionic acids are known from the literature for their biological properties; owing to the presence of the asymmetric carbon atom bonded to the naphthyl nucleus, they can exist both in the form of racemic mixtures and in the form of the corresponding d or l optically active isomers.

The d isomer of the compound of formula 1 in which $R_1$ represents the methyl radical and $R_2$ represents an hydrogen atom, namely the d-2-(6-methoxy-2-naphthyl)-propionic acid described in U.S. Pat. No. 3,904,682 and internationally known as naproxen (INN-=International Nonproprietary Name), holds a noteworthy importance for its very good antiinflammatory properties.

Its preparation has been reported many times in the literature, mainly in the patent literature. Usually these methods contemplate the synthesis of d,l-2-(6-methoxy-2-naphthyl)-propionic acid, or a precursor thereof, and the subsequent resolution into the optical antipodes via formation of salts with optically active organic bases like cinchonidine, dehydroabietylamine, N-methyl-D-glucamine, N-alkyl-D-glucamins (see French Publication 2,035,846 and U.S. Pat. Nos. 3,683,015; 4,246,164; 4,246,193 and 4,423,244). All of these resolution methods possess more or less severe drawbacks. As an example, it is often necessary to carry out several recrystallizations for obtaining the salt of the desired isomer in the wanted purity degree; in addition, the purity degree of the mixture to be resolved remarkably influences the resolution itself.

The sterospecific synthesis of naproxen and, in general, of the optically active α-naphthyl-propionic acids (see European laid open application Nos. 81993 and 110671) has been tried for avoiding these drawbacks. To our experience, however, these procedures appear to involve a lot of problems, like the use of Grignard's reagents, the optical purity not always sufficiently high and the need to use optically active intermediates.

Therefore there is still the need of technically and economically valid resolution methods of the α-naphthyl-propionic acids.

SUMMARY OF THE INVENTION

The present invention refers to a new process for the optical resolution of substantially racemic mixtures of α-naphthyl-propionic acids of formula

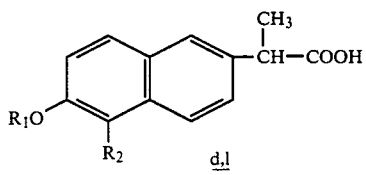

Briefly, said process comprises reacting a substantially racemic mixture of an α-naphthyl-propionic substrate of formula

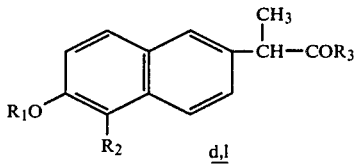

with the d or l enantiomer of a β-amino alcohol of formula $$R_4-NH_2 \quad \quad III$$

in order to obtain a pair of diastereoisomeric amides of formula

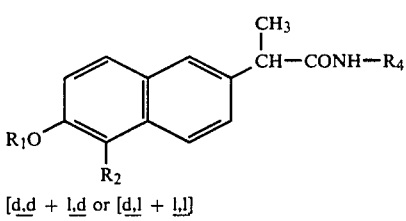

The pair of diastereoisomeric amides is then resolved in an almost quantitative way into one of the single diastereoisomeric amides by treatment with a molar excess of a strong base in a suitable solvent or solvent system. This amide is subsequently transformed into the desired optically active α-naphthyl-propionic acid by means of acid hydrolysis.

The process which is the object of the present invention can be illustrated by the following scheme

SCHEME 1

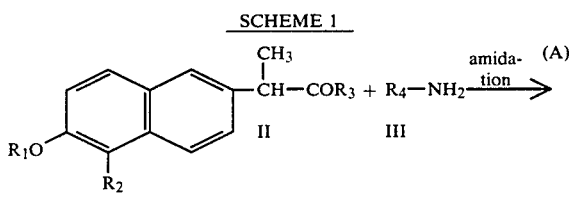

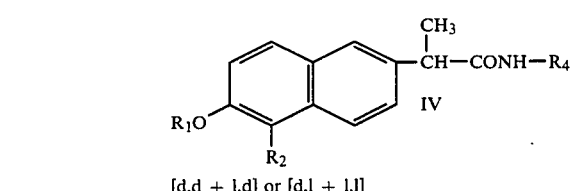

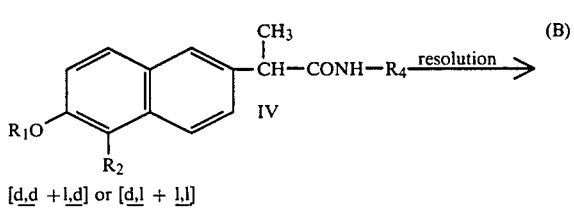

-continued
SCHEME 1

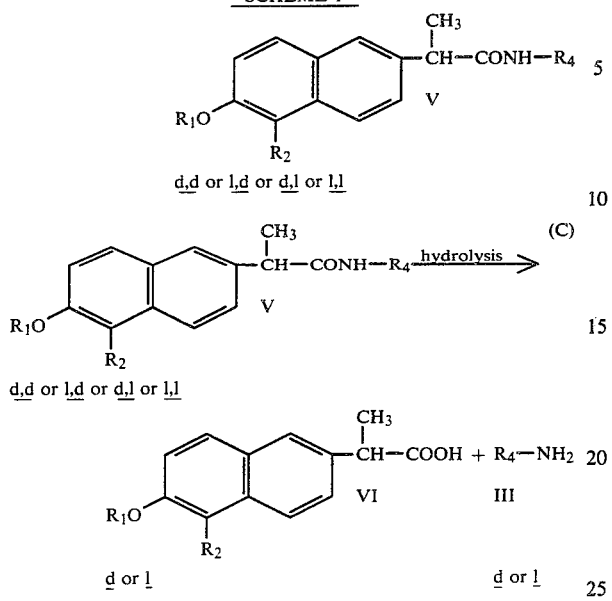

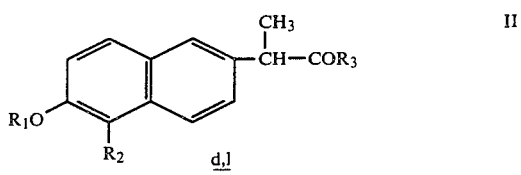

reoisomeric amides by reacting a substantially racemic mixture of an α-naphthyl-propionic substrate of formula wherein R₁, R₂ and R₃ are defined as above, with a compound of formula R₄—NH₂, represented by the d or l form of an optically active β-aminoalcohol.

Many optically active β-aminoalcohols proved to be useful for the purposes of the invention and, consequently, the aim of the here described resolution process cannot be limited by the selection of the compound of formula R₄—NH₂.

Optically active β-aminoalcohols which gave very satisfactory results were:

d and l-2-amino-1-propanol, d and l-2-amino-1-butanol, d and l-2-amino-3-methyl-1-butanol, d and l-2-amino-4-methyl-1-pentanol, d and l-2-amino-1-pentanol, d and l-2-amino-1-hexanol, d and l-2-amino-1-heptanol, d and l-2-amino-1-octanol, d and l-2-amino-3,3-dimethyl-1-butanol, d and l-1-amino-2-propanol, d and l-1-amino-2-butanol, d and l-1-amino-3-methyl-2-butanol, d and l-1-amino-3,3-dimethyl-2-butanol, d and l-1-amino-2-pentanol, d and l-1-amino-4-methyl-2-pentanol, d and l-1-amino-2-hexanol, d and l-1-amino-2-heptanol, d and l-1-amino-2-octanol, d and l-2-amino-2-phenylethanol, d and l-2-amino-2-(4-hydroxyphenyl)-ethanol, d and l-2-amino-1-phenylethanol, d and l-2-amino-2-(3-hydroxyphenyl)-ethanol, d and l-2-amino-3-phenyl-1-propanol, d and l-2-amino-3-(4-hydroxyphenyl)-1-propanol, d and l-2-amino-2-(1-naphthyl)-ethanol, d and l-2-amino-1-(3,4-dihydroxyphenyl)-ethanol and d and l-2-amino-1-(4-hydroxy-3-methoxyphenyl)-ethanol.

Preferred optically active β-aminoalcohols which give particularly satisfactory results are those in which R₄ represents the moiety

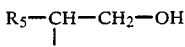

or the moiety

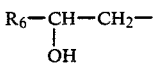

and R₅ and R₆ are alkyl radicals, straight or branched, containing from 1 to 6 carbon atoms.

Other optically active β-aminoalcohols corresponding to the general formula R₄—NH₂, in which R₄ is defined as above, fall within the purposes of the present invention even though they have not been expressly mentioned herein.

In practice a molar amount of a substantially racemic mixture of a compound of formula II is reacted with from about 1 to about 10 molar equivalents of an optically active d and l-β-aminoalcohol of formula III, optionally in presence of an organic solvent, at a tem- In the above formulas from I to VI, R₁ represents an alkyl radical having from 1 to 6 carbon atoms;

R₂ represents an hydrogen atom or an halogen atom;

R₃ represents a group selected from halogen, alkoxy containing from 1 to 8 carbon atoms, alkoxy containing from 1 to 8 carbon atoms substituted by halogen or phenyl or both, aliphatic acyloxy containing from 2 to 6 carbon atoms, benzoyloxy, substituted benzoyloxy, sulfonyloxy, benzenesulfonyloxy, 4-methylbenzenesulfonyloxy, 2-imidazolylcarbonyloxy;

R₄ is the residue of a primary or secondary alcohol which, taken together with the —NH₂ radical, forms an optically active d- or l-β-aminoalcohol, and is selected from the groups

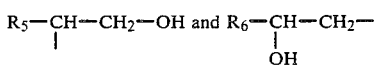

wherein R₅ may represent an alkyl, straight or branched, containing from 1 to 6 carbon atoms, a primary hydroxyalkyl containing from 1 to 4 carbon atoms, phenyl, hydroxyphenyl, phenylmethyl, hydroxyphenylmethyl, naphthyl and indolyl, and R₆ may represent an alkyl, straight or branched, containing from 1 to 6 carbon atoms, phenyl, hydroxyphenyl, dihydroxyphenyl and (4-hydroxy-3-methoxy)-phenyl.

Furthermore the first letter of each of the pair of symbols d,d, l,d, d,l or l,l related to the diastereoisomeric amides of formula IV and V, refers to the α-naphthyl-propionic acid residue, while the second letter refers to the aminoalcoholic residue.

The starting substrate of formula II preferred for the fulfillment of the present invention is that in which R₁ is an alkyl, straight or branched, containing from 1 to 6 carbon atoms, R₂ is an atom of hydrogen or of an halogen and R₃ is selected between an halogen and an alkoxy group, optionally substituted by an halogen or by a phenyl or by both, containing from 1 to 8 carbon atoms.

According to the above reported Scheme 1, the first step of the invention is the formation of a pair of diasteperature comprised between the ambient temperature and the boiling temperature of the reaction mixture.

Many solvents are suitable for this reaction, for instance, linear or ciclyc hydrocarbons having from 6 to 9 carbon atoms, aromatic hydrocarbons like benzene, toluene, the xylenes, nitrobenzene and analogs, halogenated hydrocarbons containing from 1 to 4 carbon atoms like methylchloride, methylenechloride, chloroform, carbon tetrachloride, bromoform, methylene bromide, 1,1,2,2-tetrachloroethane and analogs, mono- and di-alkyl amides, aliphatic ketones, tetrahydrofuran, dihydropyran, tetrahydropyran, ethylene or propylene glycols and the corresponding mono- or di-($C_{1-2}$)alkyl ethers, ethylacetate, butylacetate and analogs, and mixtures thereof.

Preferred solvents are the aromatic hydrocarbons and the halogenated hydrocarbons containing from 1 to 4 carbon atoms.

The temperature at which the amidation reaction is carried out is not critical and may vary within about the room temperature and the boiling temperature of the reaction mixture. It was experimentally observed that when the starting substrate of formula II is an halide ($R_3$=halogen), the reaction runs satisfactorily at ambient temperature, whereas higher reaction temperatures are required when in the starting compound of formula II $R_3$ represents an alkoxy radical, having from 1 to 8 carbon atoms and optionally substituted by halogen or phenyl or both. However the requisite temperatures can be lowered if the reaction is carried out in the presence of a strong base like quaternary ammonium hydroxides, an alkali or earth alkali hydride or amide, or an alkali ($C_{1-4}$)alkoxide. The alkali agent can be added in amounts varying within wide limits, preferably it is added in molar amounts comprised between about 3 and about 15 molar percent of the compound of formula II. In this case the amidation reaction advantageously takes place at a temperature comprised between the ambient temperature and about 50° C.

When an α-naphthyl-propionic acid halide is the substrate of formula II, the presence of an organic base may be necessary in order to block the acidity which forms during the reaction course. Said organic base may be the optically active d- or l-β-aminoalcohol itself or a tertiary organic base like the tri-($C_{1-4}$)alkylamines, pyridine, the pycolines and the like.

The yields of these reactions are practically quantitative and in any case never lower than 80%. A pair of diastereoisomeric amides of formula

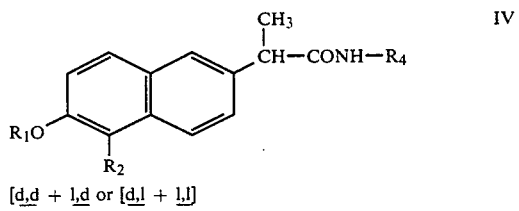

[d,d + l,d] or [d,l + l,l]

wherein $R_1$, $R_2$ and $R_4$ are as above defined, is formed, which, depending on whether the used optically active β-aminoalcohol is the d-isomer or the l-isomer, can be the pair [d,d+l,d] or the pair [d,l+l,l]. The so obtained pair of diastereoisomeric amides can be isolated and characterized, if desired. Or, the resolution into the single diastereoisomeric amides can directly take place in the same reaction ambient according to step (B) of the Scheme 1.

The resolution is performed by dissolving or suspending a pair of diastereoisomeric amides of formula IV, [d,d+l,d] or [d,l+l,l] in a suitable solvent or solvent system like, for instance, an aromatic hydrocarbon, an halogenated hydrocarbon containing from 1 to 4 carbon atoms, alcohols containing from 1 to 6 carbon atoms, mono- and di-alkylamides, aliphatic ketones, tetrahydrofuran, dihydropyran, tetrahydropyran and analogs or their mixtures. The solution or suspension is heated, at a temperature comprised between 50° C. and the boiling temperature of the mixture, then it is brought to a predetermined temperature and it is added with at least a molar amount of a strong alkali base. Subsequently the reaction mixture is kept at a temperature comprised between that at which the strong alkali base has been added and the boiling temperature of the reaction mixture for a period of time comprised from between about 30 minutes and about 12 hours. The temperature interval at which the addition of the strong alkali base takes place is not critical and essentially depends on the solvent or solvent system used; for instance when the solvent is an aromatic hydrocarbon like toluene, the addition of the alkali agent takes place at a temperature comprised between 50° and 80° C. Suitable alkali agents proved to be the alkali alkoxides like sodium and potassium methoxides, sodium ethoxide, sodium isopropoxide, potassium tert-butoxide and analogs, the quaternary ammonium hydroxides, the alkali and heart-alkali hydrides like the sodium, potassium, calcium and magnesium hydrides, the alkali and heart-alkali amides like sodium amide, potassium amide, calcium amide and analogs. The amount of alkali base used may vary within wide ranges; preferably from about 1 to about 2 molar equivalents of alkali bases are used for each molar equivalent of the pair of the diastereoisomeric amides to be resolved. The addition of the alkali base is preferably carried out under an inert gas atmosphere, for instance under nitrogen atmosphere.

The reaction mixture is heated at a temperature interval comprised between the temperature at which the addition of the base has been carried out and the boiling temperature of the reaction mixture for a period of time varying from 30 minutes and 12 hours, whereby most of the product cristallizes. A further gradual cooling completes the crystallization and the single diastereoisomeric amide of formula V can be recovered either by filtering the crystallized solid and then treating it with water or with aqueous acid or by direct addition of water or of an aqueous solution of a mineral or organic acid in the reaction medium.

The single diastereoisomeric amides d,d or l,d or d,l or l,l obtained through the described resolution method can be further purified, for instance by recrystallization from suitable solvents, e.g. those employed in the resolution procedure to which a small amount of a weak acid like, for instance, acetic acid, may be added.

The yield of single diastereoisomeric amide is exceptionally high in this process. In fact it is never lower than 85%, calculated over the starting pair of diastereoisomeric amides and not over the single diastereoisomeric amide contained in the pair. In other words, one molar amount of a pair of diastereoisomeric amides [d,d+l,d] or [d,l+l,l] is resolved with this process so as to provide not the maximum amount of the single diastereoisomer contained in the pair, namely 0.5 moles, but at least 0.85 moles.

The fact that amides made of substantially racemic mixtures of α-naphthyl-propionic acids with optically active d- or l-β-aminoalcohols could be resolved by fractional crystallization is totally new. Certain amides of racemic α-naphthyl-propionic acids are described in Dutch laid open application 75 12107 and it is also stated that they can be resolved into the corresponding optical antipodes. Concretely, however, no example is reported of amides made with whatsoever aminoalcohol and moreover this resolution could theoretically (as also here no concrete examples are reported) have taken place in a completely different manner from that described in the present process.

In Japanese Publication pre-examination No. 56 095149 an attempt is described for resolving the d,l-2-(6-methoxy-2-naphthyl)-propionic acid into the corresponding optical antipodes by subjecting to chromatographic separation a pair of two diastereoisomeric amides with an isomer of an optically active β-aminoalcohol. However also this method is completely different from the resolution process described in the present invention and moreover it appears, to the art skilled technician, a rather speculative method in view of the high costs, times and volumes involved in a chromatographic procedure carried out on industrial scale.

Furthermore it must be pointed out that with the process described in the present invention it is possible to obtain the final precursors of the optically active α-naphthyl-propionic acids of formula

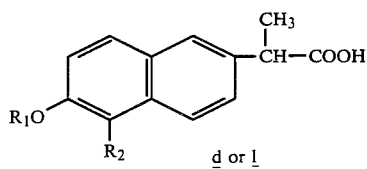

VI d or l with yields absolutely higher than those obtained with the classical resolution methods known from the literature. In fact, in none of these procedures, all based on the formation of pairs of diastereoisomeric salts with optically active organic bases, the desired single diastereoisomeric salt is obtained with a yield higher than 50% calculated over the pair of diastereoisomeric salts which must be resolved.

In the process object of the present invention, the desired diastereoisomeric amide, precursor of the acid of formula VI, is always obtained with yields higher than 85% calculated over the pair of the starting diastereoisomeric amides. In a representative, though not limitative, example in which in the pair of diastereoisomeric amides of formula IV $R_1$ is methyl, $R_2$ is hydrogen and $R_4$ is the alcoholic residue of the l-2-amino-1-butanol, the employed base is sodium methoxide and the solvent is a mixture of toluene and methanol, the N-[l-2-(1-hydroxy)-butyl]d-2-(6-methoxy-2-naphthyl)-propionamide was obtained with a yield of 94%, calculated over the pair of the starting diastereoisomeric amides.

Considering also that the yields of the subsequent hydrolysis (step C) are always higher than 90%, it derives that the present invention provides a new and useful method for the preparation of optically active α-naphthyl-propionic acids.

To obtain the final compounds of formula VI, the single diastereoisomeric amide of formula V obtained as under (step B) is subjected to acidic hydrolysis, as an example by means of concentrated or diluted mineral acids and, if necessary, to a further purification in order to obtain the desired end product with the maximum purity degree.

When in the compound of formula VI $R_2$ represents halogen, it is possible to catalytically substitute it with an hydrogn atom, for instance, by means of the hydrogenation procedure described in U.S. Pat. No. 4,423,244.

The following examples are provided for with the purpose of better illustrating the invention. The determination of the optical rotatory power was carried out by means of a Perkin Elmer 241 apparatus. The starting substrates of formula II were prepared according to known literature methods. The optically active β-aminoalcohols of formula III are commercial products or were prepared according to known literature methods.

EXAMPLE 1

N-[d-2-(1-Hydroxy)-butyl]-d,l-2-(6-methoxy)-2-naphthyl)-propionamide[d,d+l,d]

203 Grams (0.815 moles) of d,l-2-(6-methoxy-2-naphthyl)-propionic acid chloride in 500 ml of methylene chloride are dripped into a solution of 164 ml (1.74 moles) of d-2-amino-1-butanol in 1000 ml of methylene chloride while keeping the temperature at +20° C. 15 minutes after the end of the dripping, the reaction mixture is added with 1000 ml of water and acidified. The organic layer is separated, washed with water until neutrality and subsequently dried over sodium sulfate. After evaporation of the solvent, an oily residue is obtained, which is taken up with 500 ml of tetrachloroethylene. Upon filtration 213.9 g (87%) of the title compound are obtained. $[\alpha]_D^{20} = -32.5°$ (C=1% in methanol), m.p. 105°–126.5° C.

EXAMPLE 2

N-[l-2-(1-Hydroxy)-butyl]-d,l-2-(6-methoxy-2-naphthyl)-propionamide[d,l−l,l]

A solution of 200 g (0.803 moles) of d,l-2-(6-methoxy-2-naphthyl)-propionic acid chloride in 500 ml of methylene chloride is dripped into a solution of 73.8 ml (0.78 moles) of l-2-amino-1-butanol and 108.7 ml (0.78 moles) of triethylamine in 500 ml of methylene chloride, at room temperature. After 30 minutes, the reaction mixture is added with 1000 ml of water, whereby a solid begins to form. This solid is dissolved by gentle heating, the solution is then cooled, the organic layer is separated, washed with water and dried over sodium sulfate. After evaporating the solvent, a residue is obtained, which is worked up as described in the foregoing Example. Yield: 205.4 g (85%) of the title compound. $[\alpha]_D^{20} = +32.2°$ (C=1% in methanol), m.p. 102°–125° C.

EXAMPLE 3

N-[l-2-(1-Hydroxy)-butyl]-d,l-2-(6-methoxy-2-naphthyl)-propionamide[d,l+l,l]

10 Grams (0.041 moles) of d,l-2-(6-methoxy-2-naphthyl)-propionic acid methyl ester are admixed with 20 ml (0.212 moles) of l-2-amino-1-butanol and the resulting mixture is heated for 8 hours at 130° C. under nitrogen atmosphere. After cooling to room temperature and adding 100 ml of water, the solution is acidified. A solid is obtained, which is filtered, washed with water and recrystallized from tetrachloroethylene. Yield: 10.7 g (86.8%). $[\alpha]_D^{20} = +32.1°$ (C=1% in methanol).

EXAMPLE 4

N-[d-2-(1-Hydroxy)-butyl]-d,l-2-(5-bromo-6-methoxy-2-naphthyl)-propionamide[d,d+l,d]

154.6 Grams (0.471 moles) of d,l-2-(5-bromo-6-methoxy-2-naphthyl)-propionic acid chloride are dissolved in 500 ml of methylene chloride and the obtained solution is slowly dripped into a solution of 47.2 ml (0.50 moles) of d-2-amino-1-butanol and 104 ml (0.74 moles) of triethylamine in 500 ml of methylene chloride, while keeping the temperature at +20° C. 15 minutes after the end of the dripping the reaction mixture is added with 1000 ml of water and acidified by means of 6N aqueous hydrochloric acid, whereby a solid is obtained which is washed with water, then with methylene chloride and finally dried. Yield: 163.6 g (91.3%) of title compound. $[\alpha]_D^{20} = -25.5°$ (C=1% in methanol), m.p. 143°–147° C.

EXAMPLE 5

N-[l-2-(1-Hydroxy)-butyl]-d,l-2-(5-bromo-6-methoxy-2-naphthyl)-propionamide[d,l+l,l]

51 Grams (0.111 moles) of d,l-2-(5-bromo-6-methoxy-2-naphthyl)-propionic acid 3-bromo-2,2-dimethyl-propyl ester are suspended in 75 ml (0.795 moles) of l-2-amino-1-butanol, and the reaction mixture is heated at 130° C. for 16 hours under nitrogen atmosphere. After cooling, the reaction mixture is added with 200 ml of methylene chloride and 400 ml of water and then acidified by means of 6N hydrochloric acid. A suspension is obtained which is cooled to 10° C., the formed solid is filtered, washed first with water and then with methylene chloride and finally recrystallized from ethyl acetate. Yield: 34 g (80.6%) of title product. $[\alpha]_D^{20} = +25.4°$ (C=1% in methanol), m.p. 143°–146° C.

EXAMPLE 6

N-[d-2-(1-Hydroxy)-butyl]-d,l-2-(6-methoxy-2-naphthyl)-propionamide[d,d+l,d]

90 Grams (0.37 moles) of d,l-2-(6-methoxy-2-naphthyl)-propionic acid methyl ester are poured into 360 ml of anhydrous toluene and the obtained mixture is refluxed for 30 minutes, whereby 45 ml of solvent are distilled off. After cooling to 90° C. and adding 45 ml (0.47 moles) of d-2-amino-1-butanol, the resulting solution is again refluxed for 30 minutes and further 45 ml of toluene are distilled off. The reaction mixture is then cooled to 25° C. and added, under nitrogen atmosphere, with 8 ml (0.043 moles) of a 30% (w/w) methanol solution of sodium methoxide and stirred overnight at room temperature. After adding 180 ml of a 3% aqueous solution of hydrochloric acid and heating at 80° C. for 15 minutes, the reaction mixture is cooled to 5° C. and the solid which precipitates is filtered, washed first with water and then with toluene and finally dried in vacuo to give 108 g of product identical with that obtained in Example 1. The yield, calculated over the methyl ester, is of 96% on theoretical.

EXAMPLE 7

N-[l-2-(1-Hydroxy)-butyl]-d-2-(6-methoxy-2-naphthyl)-propionamide[d,l]

A suspension containing 50 g (0.166 moles) of N-[l-2-(1-hydroxy)-butyl]-d,l-2-(6-methoxy-2-naphthyl)-propionamide in 500 ml of anhydrous toluene is heated, under nitrogen atmosphere, to 50° C. and then is added with 34 ml of a 30% (w/w) solution of sodium methoxide (0.189 moles) in methanol. An initial solubilization takes place followed by a crystallization; the reaction mixture is kept at 50° C. for an hour under stirring and then the temperature is increased while distilling off the solvent until 105° C. are attained. Subsequently the reaction mixture is cooled to 40° C., is added with 200 ml of water, is heated to 50° C. and then cooled to 5° C. obtaining a plentiful precipitate which is filtered, washed with water and with toluene and lastly is dried under vacuum. 47 Grams of pure N-[l-2-(1-hydroxy)-butyl]-d-2-(6-methoxy-2-naphthyl)-propionamide[d,l] which shows $[\alpha]_D^{20} = +33°$ (C=1% in methanol) and m.p.=125°–126° C. are obtained; the TLC does not show the presence of the other diastereoisomer. The yield, calculated over the mixture of the starting diastereoisomeric amides, is equivalent to 94%.

EXAMPLE 8

N-[d-2-(1-Hydroxy)-butyl]-l-2-(6-methoxy-2-naphthyl)-propionamide[l,d]

A suspension containing 50 g (0.166 moles) of N-[d-2-(1-hydroxy)-butyl]-d,l-2-(6-methoxy-2-naphthyl)-propionamide in 500 ml of anhydrous toluene is heated, under nitrogen atmosphere, to 50° C. and then is added with 8.17 g (0.151 moles) of sodium methoxide powder and with 5.8 ml (0.032 moles) of a 30% (w/w) solution of sodium methoxide in methanol. The reaction mixture is kept at 70° C. for an hour under stirring, then it is cooled to 50° C. and is added with 200 ml of water. The mixture is cooled to about 5° C. and after an hour the precipitated solid is filtered, is washed with water and with toluene and is dried under vacuum obtaining 46.5 g of pure N-[d-2-(1-hydroxy)-butyl]-l-2-(6-methoxy-2-naphthyl)-propionamide[l,d] which shows $[\alpha]_D^{20} = -33.5°$ (C=1% in methanol) and m.p.=123°–124° C.; the TLC does not show the presence of the other diastereoisomer. The yield, calculated over the mixture of the starting diastereoisomeric amides, is equivalent to 93%.

EXAMPLE 9

N-[l-2-(1-Hydroxy)-butyl]-d-2-(5-bromo-6-methoxy-2-naphthyl)-propionamide[d,l]

40 Grams (0.105 moles) of N-[l-2-(1-hydroxy)-butyl]-d,l-2-(5-bromo-6-methoxy-2-naphthyl)-propionamide are suspended in 600 ml of toluene and are heated to the boiling temperature eliminating 200 ml of solvent by distillation. Subsequently it is cooled to 60° C. and, under nitrogen atmosphere, 4 ml of methanol and 6 g (0.111 moles) of sodium methoxide are added. The reaction mixture is kept for an hour at 60° C. under stirring, then it is cooled to 30° C. and it is added with 200 ml of water and after 30 minutes of stirring at this temperature it is cooled to 2° C. The crystalline precipitate is then filtered, washed with water and with toluene and dried under vacuum. 37.4 Grams of pure N-[l-2-(1-hydroxy)-butyl]-d-2-(5-bromo-6-methoxy-2-naphthyl)-propionamide having $[\alpha]_D^{20} = +18.9°$ (C=1% in methanol) and m.p.=153°–155° C. are obtained. The TLC does not show the presence of the other diastereoisomer.

The yield, calculated over the mixture of the starting diastereoisomeric amides, is equivalent to 93.5%.

EXAMPLE 10

N-[l-2-(1-Hydroxy)-butyl]-d-2-(5-bromo-6-methoxy-2-naphthyl)-propionamide[d,l]

112 Grams (0.306 moles) of d,l-2-(5-bromo-6-methoxy-2-naphthyl)-propionic acid n-butyl ester and 31.73 g (0.356 moles) of l-2-amino-1-butanol are put in 800 ml of anhydrous toluene, the reaction mixture is heated to 50° C. and, under nitrogen atmosphere, is added with 10 ml of methanol and with 21.8 g (0.404 moles) of sodium methoxide. The reaction mixture is heated to 70° C. and 150 ml of solvent are distilled off under a light vacuum. Subsequently the reaction mixture is cooled to 30° C., is added with 300 ml of water and after 30 minutes of stirring at this temperature it is further on cooled to 5° C. and the precipitate is filtered. The solid is washed on the filter first with water and then with toluene and subsequently is dried under vacuum. 105 Grams of pure N-[l-2-(Hydroxy)-butyl]-d-2-(5-bromo-6-methoxy-2-naphthyl)-propionamide having $[\alpha]_D^{20} = +18.9°$ (C=1% in methanol) and m.p.=153°-155° C. are obtained; the TLC does not show the presence of the other diastereoisomer. The yield, calculated over the racemic mixture of the n-butyl ester of the d,l-2-(5-bromo-6-methoxy-2-naphthyl)-propionic acid, is equivalent to 90%.

EXAMPLE 11

N-[d-2-(1-Hydroxy)-butyl]-l-2-(5-bromo-6-methoxy-2-naphthyl)-propionamide[l,d]

By operating in a way similar to that described in Example 10, by using the d-2-amino-1-butanol instead of the l-2-amino-1-butanol, 102.7 g of pure N-[d-2-(1-hydroxy)-butyl]-l-2-(5-bromo-6-methoxy-2-naphthyl)-propionamide having $[\alpha]_D^{20} = -19°$ (C=1% in methanol) and p.m.=152°-154° C. are obtained; the TLC does not show the presence of the other diastereoisomer. The yield, calculated over the racemic mixture of the starting ester, is equivalent to 88%.

EXAMPLE 12

N-[l-2-(1-Hydroxy)-butyl]-d-2-(5-bromo-6-methoxy-2-naphthyl)-propionamide[d,l]

20 Grams (0.052 moles) of N-[l-2-(1-hydroxy)-butyl]-d,l-2-(5-bromo-6-methoxy-2-naphthyl)-propionamide are suspended in 300 ml of toluene and the reaction mixture is heated to the boiling temperature while distilling off 100 ml of solvent. Subsequently the reaction mixture is cooled to 70° C. under nitrogen atmosphere and is added with 14 ml (0.077 moles) of a 30% (w/w) solution of sodium methoxide in methanol. The temperature is kept at 50° C. for about two hours eliminating about 20 ml of condensate. Subsequently the reaction mixture is cooled to 10° C., is added with 100 ml of water, is heated to 55° C. and lastly it is slowly cooled to ambient temperature. The precipitated solid is filtered, first washed with water and then with toluene and dried under vacuum. 17.4 Grams of pure N-[l-2-(1-hydroxy)-butyl]-d-2-(5-bromo-6-methoxy-2-naphthyl)-propionamide[d,l] having $[\alpha]_D^{20} = +18.9°$ (C=1% in methanol) and m.p.=153°-155° C. are obtained; the TLC does not show the presence of the other diastereoisomer. The yield, calculated over the mixture of the starting diastereoisomeric amides, is equivalent to 87%.

EXAMPLE 13

N-[l-2-(1-hydroxy)-butyl]-d-2-(5-bromo-6-methoxy-2-naphthyl)-propionamide[d,l]

A suspension containing 20 g (0.052 moles) of N-[l-2-(1-hydroxy)-butyl]-d,l-2-(5-bromo-6-methoxy-2-naphthyl)-propionamide in 300 ml of toluene is heated to reflux distilling off 100 ml of solvent. Then, under nitrogen atmosphere, the reaction mixture is cooled to 50° C. and is added with 4 ml of methanol and 7.4 g (0.066 moles) of potassium tert.-butoxide. The reaction mixture is kept at 50° C. under stirring for three hours, then it is cooled to 30° C., is added with 100 ml of water and is kept under stirring at this temperature for about 30 minutes. After having further on cooled the reaction mixture to 20° C., the precipitate solid is filtered, washed with water and with toluene and dried under vacuum. 18.3 Grams of pure N-[l-2-(1-hydroxy)-butyl]-d-2-(5-bromo-6-methoxy-2-naphthyl)-propionamide[d,l] having $[\alpha]_D^{20} = +18.9°$ (C=1% in methanol) and m.p.=153°-155° C. are obtained; the TLC does not show the presence of the other diastereoisomer. The yield, calculated over the mixture of the starting diastereoisomeric amides, is equivalent to 91.5%.

EXAMPLE 14

N-[d-2-(1-hydroxy)-butyl]-l-2-(5-bromo-6-methoxy-2-naphthyl)-propionamide[l,d]

20 Grams (0.052 moles) of N-[d-2-(1-hydroxy)-butyl]-d,l-2-(5-bromo-6-methoxy-2-naphthyl)-propionamide are suspended in 300 ml of toluene and the mixture is heated to reflux distilling off 100 ml of solvent. Then, under nitrogen atmosphere, the reaction mixture is cooled to 70° C. and is added with 2 ml of methanol and 3.1 g (0.057 moles) of sodium methoxide and the temperature is kept at 70° C. for an hour. The reaction mixture is subsequently cooled to ambient temperature, then it is added with 100 ml of water and with 5 ml of 32% aqueous hydrochloric acid, it is further on cooled to 5° C. and the solid is recovered by filtration, washed with water and dried under vacuum to give 18 g of a single diastereoisomeric amide[l,d], which is TLC does not show the presence of the other diastereoisomer, with a yield of 90% calculated over the racemic mixture of diastereoisomeric amides. $[\alpha]_D^{20} = -18.9°$ (C=1% is methanol), m.p.=153°-155° C.

EXAMPLE 15 d-2-(6-Methoxy-2-naphthyl)-propionic acid

30 Grams (0.1 moles) of N-[l-2-(1-hydroxy)-butyl]-d-2-(6-methoxy-2-naphthyl)-propionamide are suspended in a mixture made of 140 ml of water and 22 ml of 48% (w/w) sulfuric acid and the resulting suspension is heated under stirring at 98° C. for 13 hours. After cooling to 60° C., the solid is filtered, washed with water at 50° C., suspended in 150 ml of water and brought to pH 10 by means of a 30% (w/w) aqueous solution of sodium hydroxide. The so obtained solution is twice extracted with 25 ml of methylene chloride. The aqueous layer is added with 100 ml of water and then filtered. The clear filtrate is heated to 40° C. and is slowly acidified to pH 3 with aqueous 6N hydrochloric acid. The obtained suspension is heated to 60° C. for 15 minutes and then is filtered. The solid is washed with hot water at 60° C. and dried under vacuum. 20.2 Grams (yield 88%) of pure d-2-(6-methoxy-2-naphthyl)-propionic acid having $[\alpha]_D^{20} = +66°$ (C=1% in chloroform) are obtained.

EXAMPLE 16 d-2-(5-Bromo-6-methoxy-2-naphthyl)-propionic acid

74 Grams (0.194 moles) of N-[1-2-(1-hydroxy)-butyl]-d-2-(5-bromo-6-methoxy-2-naphthyl)-propionamide are suspended in a mixture of 273 ml of water and of 29.32 ml of 32% (w/w) aqueous hydrochloric acid and are heated to reflux for 24 hours. The suspension is cooled to 40° C. and filtered. The solid is washed with water at 40° C., suspended in 400 ml of water and brought to pH 10 by means of a 30% (w/w) aqueous solution of sodium hydroxide. The so obtained solution is extracted three times with 50 ml of methylene chloride and filtered. The so obtained clear solution is heated to 50° C. and is slowly brought to pH 3 by means of 32% (w/w) aqueous hydrochloric acid. The reaction mixture is kept under stirring at this temperature for 30 minutes, is filtered and the solid is washed with 100 ml of water at 50° C. and is dried under vacuum. 54.6 Grams of pure product having $[\alpha]_{578}^{20} = +46.7°$ (C=1% in chloroform) are obtained with a yield of 91%.

I claim:

1. A process for the optical resolution of a racemic mixture of α-naphthyl-propionic acids of formula

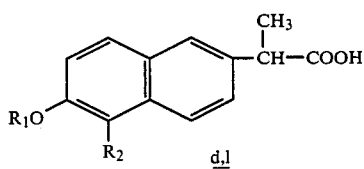

wherein $R_1$ is straight or branched alkyl having from 1 to 6 carbon atoms and $R_2$ is hydrogen or halogen, which comprises the steps of:

(A) reacting a substantially racemic substrate of formula

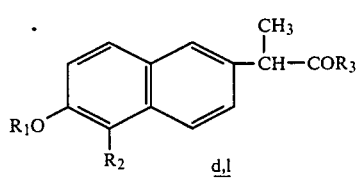

wherein $R_1$ and $R_2$ are as defined above and $R_3$ is a member selected from the group consisting of halogen, alkoxy containing from 1 to 8 carbon atoms, alkoxy containing from 1 to 8 carbon atoms substituted by halogen or phenyl or both, halogen and phenyl, aliphatic acyloxy containing from 2 to 6 carbon atoms, benzoyloxy, substituted benzoyloxy, sulfonyloxy, benzenesulfonyloxy, with a substance of formula $R_4$—$NH_2$  III wherein $R_4$ is the residue of a primary or secondary alcohol which, taken together with the —$NH_2$ radical, forms an optically active β-aminoalcohol, and has the formula,

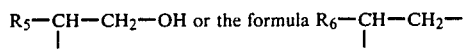

wherein $R_5$ is straight or branched alkyl, containing from 1 to 6 carbon atoms, primary hydroxyalkyl containing from 1 to 4 carbon atoms, phenyl, hydroxyphenyl, phenylmethyl, hydroxyphenylmethyl, naphthyl or indolyl and $R_6$ is straight or branched alkyl, containing from 1 to 6 carbon atoms, phenyl, hydroxyphenyl, dihydroxyphenyl and (4-hydroxy-3-methoxy)-phenyl, at a temperature between about room temperature and the boiling temperature of the reaction mixture, to obtain a pair of disatereoisomeric amides of formula

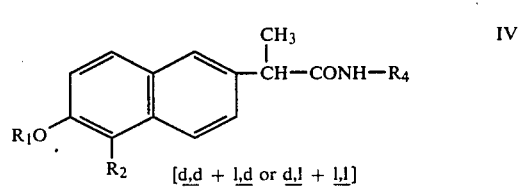

wherein $R_1$, $R_2$ and $R_4$ are as defined above;

(B) resolving said pair of diastereoisomeric amides into a single distereoisomeric amide by heating at a predetermined temperature a molar amount of the pair of diastereoisomeric amides in a solvent or solvent system and adding at least a molar amount of a strong alkali agent, heating at a temperature between the temperature at which said alkali agent has been added and the boiling temperature of the reaction mixture for a period of time between 30 minutes and 12 hours and then gradually lowering the temperature to aid the crystallization whereby the desired single diasteroisomeric amide of formula

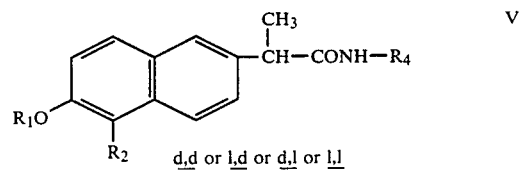

is recovered, wherein $R_1$, $R_2$ and $R_4$ are as defined above, by filtration of the crystallized residue and subsequent treatment with water or by addition to the reaction mixture of an aqueous acidic solution, or water or of an aqueous solution of a mineral or organic acid, and (c) subjecting the so obtained single diastereoisomeric amide to acid hydrolysis, thus recovering a compound of formula

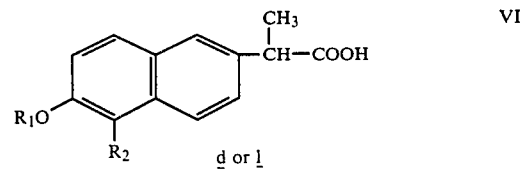

in which $R_1$ and $R_2$ are as defined hereinabove.

2. The process according to claim 1 wherein said step (A) is carried out in the presence of an organic solvent.

3. The process according to claim 1, wherein said step (A) is carried out in the presence of a base.

4. The process according to claim 1, wherein in said compound of formula VI, $R_2$ is halogen and said compound of formula VI is catalytically reduced to obtain said compound of formula VI wherein $R_2$ is H.

5. The process according to claim 1, wherein in said compound of formula II, $R_1$ is straight or branched alkyl containing from 1 to 6 carbon atoms, $R_2$ is hydrogen or halogen, and $R_3$ is a member selected from the group consisting of halogen, alkoxy containing from 1 to 8 carbon atoms, and alkoxy containing from 1 to 8 carbon atoms substituted by halogen or phenyl or both halogen and phenyl.

6. The process according to claim 1, wherein in said optically active β-aminoalcohol of formula $R_4$—$NH_2$, $R_4$ is

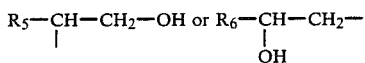

and $R_5$ and $R_6$ are straight or branched alkyl containing from 1 to 6 carbon atoms.

7. The process according to claim 6, wherein in said optically active β-aminoalcohol of formula $R_4$—$NH_2$, $R_4$ is

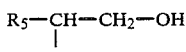

and $R_5$ is ethyl.

8. The process according to claim 6, wherein said optically active β-aminoalcohol is l-2-amino-1-butanol.

9. The process according to claim 1, wherein in step (A) each molar amount of said compound of formula II is reacted with from 1 to 10 molar amounts of said optically active β-aminoalcohol of formula III.

10. The process according to claim 2, wherein step (A) is carried out in the presence of an organic solvent which is a member selected from the group of linear and cyclic hydrocarbons containing from 6 to 9 carbon atoms, aromatic hydrocarbons, halogenated hydrocarbons containing from 1 to 4 carbon atoms, mono- and di-alkylamides aliphatic ketones, tetrahydrofuran, dihydropyran, tetrahydropyran, ethylene or propylene glycols and the corresponding mono- or di-alkyl ethers containing 1 or 2 carbon atoms, ethyl acetate, butyl acetate and mixtures thereof.

11. The process according to claim 1, wherein step (B) is carried out in the presence of a solvent which is a member selected from the group consisting of aromatic hydrocarbons, halogenated hydrocarbons containing from 1 to 4 carbon atoms, alcohols containing from 1 to 6 carbon atoms, mono- and di-alkylamides, aliphatic ketones, tetrahydrofuran, dihydropyran, tetrahydropyran and mixtures thereof.

12. The process according to claim 1, wherein step (B) is performed in the presence of a strong alkaline agent which is a member selected from the group consisting of quaternary ammonium hydroxides, alkali lower alkoxides and alkali or alkaline earth hydrides and amides.

13. The process according to claim 9, wherein the alkaline agent is an alkali lower alkoxide.

14. The process according to claim 12, wherein the amount of the alkaline agent is at least a molar equivalent for each molar equivalent of the racemic mixture of diastereoisomeric amides.

15. An amide which is:
(a) (N-[l-2-(1-hydroxy)-butyl]-d-2-(6-methoxy-2-naphthyl)-propionamide;
(b) (N-[d-2-(1-hydroxy)-butyl]-l-2(6-methoxy-2-naphthyl propionamide;
(c) (N-[l-2-(1-hydroxy)-butyl]-d-2-(5-bromo-6-methoxy-2-naphthyl)-propionamide; or
(d) (N-[d-2-(1-hydroxy)-butyl]-l-2-(5-bromo-6-methoxy-2-naphthyl)-propionamide.

16. The amide according to claim 15 which is (N-[l-2(1-hydroxy)-butyl]-d-2-(6-methoxy-2-naphthyl)-propionamide;

17. The amide according to claim 15 which is (N-[d-2-(1-hydroxy)-butyl]-l-2(6-methoxy-2-naphthyl)-propionamide.

18. The amide according to claim 15 which is (N-[l-2-(1-hydroxy)-butyl]-d-2-(5-bromo-6-methoxy-2-naphthyl)propionamide.

* * * * *